(12) United States Patent
Longo et al.

(10) Patent No.: US 11,406,122 B2
(45) Date of Patent: Aug. 9, 2022

(54) AUTOIMMUNITY AND MULTIPLE SCLEROSIS TREATMENT

(71) Applicant: UNIVERSITY OF SOUTHERN CALIFORNIA, Los Angeles, CA (US)

(72) Inventors: Valter D. Longo, Playa del Rey, CA (US); In Young Choi, Garden Grove, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 15/301,480

(22) PCT Filed: Apr. 2, 2015

(86) PCT No.: PCT/US2015/024021
§ 371 (c)(1),
(2) Date: Oct. 3, 2016

(87) PCT Pub. No.: WO2015/153850
PCT Pub. Date: Oct. 8, 2015

(65) Prior Publication Data
US 2017/0027217 A1    Feb. 2, 2017

Related U.S. Application Data

(60) Provisional application No. 61/974,189, filed on Apr. 2, 2014.

(51) Int. Cl.
*A23L 33/00* (2016.01)
*A61K 38/00* (2006.01)
*A61K 45/06* (2006.01)
*G01N 33/564* (2006.01)

(52) U.S. Cl.
CPC .............. *A23L 33/30* (2016.08); *A61K 38/00* (2013.01); *A61K 45/06* (2013.01); *G01N 33/564* (2013.01); *A23V 2002/00* (2013.01); *G01N 2800/285* (2013.01)

(58) Field of Classification Search
CPC .............................. A23L 33/30; G01N 33/564
See application file for complete search history.

(56) References Cited

U.S. PATENT DOCUMENTS

| | | | |
|---|---|---|---|
| 8,211,700 B2 | 7/2012 | Longo | |
| 8,728,815 B2 | 5/2014 | Longo | |
| 8,865,646 B2 | 10/2014 | Longo | |
| 9,237,761 B2 | 1/2016 | Longo et al. | |
| 9,386,790 B2 | 7/2016 | Longo et al. | |
| 2004/0121044 A1* | 6/2004 | Tiano | A23L 33/40 426/72 |
| 2011/0118528 A1* | 5/2011 | Longo | A61K 31/07 600/1 |
| 2013/0045215 A1 | 2/2013 | Longo et al. | |
| 2013/0316948 A1 | 11/2013 | Longo et al. | |
| 2014/0112909 A1* | 4/2014 | Longo | A61K 45/00 424/130.1 |
| 2014/0328863 A1 | 11/2014 | Longo | |
| 2014/0350105 A1* | 11/2014 | D'Agostino | A61K 31/20 514/547 |
| 2015/0133370 A1 | 5/2015 | Longo | |
| 2015/0250771 A1 | 9/2015 | Longo et al. | |
| 2016/0331016 A1 | 11/2016 | Longo et al. | |
| 2017/0000183 A1 | 1/2017 | Longo et al. | |
| 2017/0035094 A1 | 2/2017 | Longo et al. | |

FOREIGN PATENT DOCUMENTS

| | | |
|---|---|---|
| CN | 102753162 A | 10/2012 |
| EP | 2 353 595 A1 | 8/2011 |
| WO | 2006/118665 A2 | 11/2006 |
| WO | 2013/028555 A2 | 2/2013 |

OTHER PUBLICATIONS

Kim, PLOSone, 7, 5, 2012.*
Vining, Arch Neurol, 55, 1998.*
Walpole, BMC Public Health, 12, 439, 2012 (Year: 2012).*
Piccio, Journal of Leukocyte Biology, 84, 4, 2008 (Year: 2008).*
U.S. Appl. No. 15/297,672, filed Oct. 19, 2016, inventors: Valter D. Longo et al.; Applicant: University of Southern California, title: "Methods and Formulations Promoting Tissue/Organ Regeneration, Longevity and Healthspan", 85 pgs.
Supplemental European Search Report dated Jul. 31, 2017 for EP Appn. 15774032.5 filed Oct. 21, 2016, 8 pgs.
Chinese Office Action dated Sep. 26, 2019 for CN Appn. No. 2015800282227 filed Nov. 28, 2016, 11 pgs.
Chang, K.-A et al., "The Preventative and Therapeutic Effects of Intravenous Human Adipose-Derived Stem Cells in Alzheimer's Disease Mice," Plos ONE, Sep. 2012, 18 pgs. https://www.researchgate.net/publication/232226943.
Preliminary Examination Report dated Oct. 29, 2020 for BR Appn. No. 112016022789-1 filed Sep. 30, 2016, 7 pgs.
Miljkovic, D. et al., "Multiple Sclerosis: Molecular Mechanisms and Therapeutic Opportunities," Antioxidants & Redox Signaling (2013), v. 19, n. 18, pp. 2286-2334.
Office Action dated Apr. 14, 2021 for JP 2020-020901, 6 pgs (includes Eng Translation).

(Continued)

*Primary Examiner* — Robert A Wax
*Assistant Examiner* — William Craigo
(74) *Attorney, Agent, or Firm* — Brooks Kushman P.C.

(57) ABSTRACT

A method for alleviating a symptom of multiple sclerosis or other autoimmune or inflammatory disease includes a step of identifying a subject having multiple sclerosis or other autoimmune diseases. A fasting mimicking diet is administered to the subject for a first predetermined time period, the fasting mimicking diet providing less than 50% of the subject's normal caloric intake. A non-fasting diet is administered to the subject for a second time period following the first time period. The non-fasting diet provides the subject greater than 60 percent of the subject's normal caloric intake but a calorie intake necessary for the subject to return to a normal healthy weight.

19 Claims, 5 Drawing Sheets

(56) References Cited

OTHER PUBLICATIONS

Kang, W., "Why do these European and American diabetic patients live so long," Hebei Science and Technology Press, Aug. 2012 (Machine Translated English Abstract), 4 pgs.

Dietary Guidelines for Americans, 2015-2020, 8th Ed., HHS Publn. # HHS-ODPHP-2015-202-01DGA-A and USDA Publn # Home and Garden Bulletin No. 232, 144 pgs.

Communication dated Mar. 17, 2022 for European Appn. No. 15744032.5, 7 pgs.

* cited by examiner

Table 1. FMD-altered T cell populations and cytokines as therapeutic targets for treating major autoimmune diseases and chronic inflammatory diseases.

| | Diseases | Pathogenesis | Targets for immunotherapy | | | | | | |
|---|---|---|---|---|---|---|---|---|---|
| | | | antigen-specific | | non-antigen-specific | | | | |
| | | | CD4+ T cells | CD8+ T cells | MCP-1 | TNF-α | IL-12 | RANTES | CRP |
| Autoimmune Diseases | Graves' disease (GD) and Hashimoto's thyroiditis (chronic thyroiditis) | Defect in regulatory T cells causing expansion of CD4+ T-helper cells which when activated, secrete cytokines and activate cytotoxic (CD8+) T cells and induce thyroid cell apoptosis. | + | + | | + | | + | |
| | Rheumatoid Arthritis (RA) | Pro-inflammatory cytokines produced by the CD8+ T cells in the synovial membrane and synovial fluid, accumulate in the joint, potentiating bone degradation by stimulating osteoclasts, and further stimulating other immune cells in a vicious circle. | NA | + | | + | | | |
| | Autoimmune vitiligo | T-cell cytolytic activity targeting epidermal melanocytes cause progressive depigmentation and autoimmune vitiligo. | + | + | | + | | | |
| | Type I diabetes (T1D) | CD4+ and CD8+ T cell-dependent autoimmune process that culminates in complete destruction of insulin-producing β cells. | + | + | + | + | + | + | |
| | Autoimmune gastritis and pernicious anemia (AIG/PA) | Pathogen-induced, organ-specific autoimmunity, in which gastric H+/K+-ATPase has been recognized as the major autoantigen by autoreactive gastric CD4+ T cells leading to gastric inflammation and loss of gastric glands in the antrum and corpus. | + | - | | + | | | |
| | Multiple sclerosis (MS) | CD4+ and CD8+ T-cells dependent auto-immune process that leads to oligodendrocyte death, demyelination and axonal damage which eventually causes neurological symptoms | + | + | | + | + | + | |
| | glomerular nephritis (GN) | Antibodies-mediated and T cell-mediated autoimmunity induced inflammatory injury in the glomerulus. | + | +/- | | + | + | | |
| | Systemic lupus erythematosus (SLE) | Production of plethora of autoantibodies which drive immune-complex related inflammation in target tissues and organs. | + | + | | + | | | |
| | Sjogren's syndrome (SjS) | Infiltration of exocrine glands with T and B lymphocytes, leading to glandular dysfunction and frequently accompanied by hypergammaglobulinemia and autoantibodies. | + | + | | + | + | | |
| Chronic Inflammatory Diseases | Parkinson's Disease | Accumulation of Lewy bodies and precipitated α-synuclein, activating microglia leading to neuro inflammation and motor-neuronal deaths. | - | - | | + | + | | + |
| | Irritable Bowel Syndrome (ulcerative colitis and Crohn's disease) | Chronic inflammatory bowel disease associated with imbalanced synthesis of pro-inflammatory mediators o f the inflamed intestines. | + | + | + | + | + | ? | + |
| | Dermatitis | Inflammation of the skin caused by a delayed-type hypersensitivity mediated by T-lymphocytes | + | + | | + | | | |
| FMD TREATMENT | | | ↓ | ↓ | ↓↓ | ↓↓ | ↓↓ | ↓↓ | ↓ |

AUTOIMMUNITY AND MULTIPLE SCLEROSIS TREATMENT

CROSS-REFERENCE TO RELATED APPLICATION

This application is the U.S. national phase of PCT Appln. No. PCT/US2015/024021 filed Apr. 2, 2015 which claims the benefit of U.S. provisional application Ser. No. 61/974,189 filed Apr. 2, 2014, the disclosure of which is incorporated in its entirety by reference herein.

STATEMENT REGARDING FEDERALLY SPONSORED RESEARCH OR DEVELOPMENT

The invention was made with Government support under Contract No. PO1AGT034906 awarded by the National Institutes of Health/National Institute of Aging. The Government has certain rights to the invention.

TECHNICAL FIELD

In at least one aspect, the present invention is related to the identification of a dietary formulation and method for treating and reversing multiple sclerosis, type I diabetes and other autoimmune/inflammatory diseases and preventing a relapse of the disease in part by reducing, preventing, or reversing autoimmunity and inflammation and promoting regeneration at the lesion site.

BACKGROUND

Autoimmune diseases are a class of illnesses in which normal tissues are damaged by an abnormal immune response. T lymphocytes populations play critical roles in the immuno-pathogenesis of many autoimmune/chronic inflammatory diseases. It has been shown that both the reactive $CD4^+$ T cells and cytotoxic $CD8^+$ T cells and the related cytokines importantly contribute to the pathogenesis of major autoimmune diseases/chronic inflammatory diseases including multiple sclerosis, type 1 diabetes, HIV, Rheumatoid Arthritis, atopic dermatitis, ulcerative colitis, Crohn's disease, psoriasis, Parkinson's disease, irritable bowel syndrome, asthma, and hepatitis.

These autoimmune/inflammatory diseases often occur by T-cell mediated attack of a subject own cell-types but they can also involve a variety of cytokines that can directly cause damage to cells, tissues and organs including TNF and interleukins. Antibodies, vaccines, cytokines, chemicals and stem cell transplantation that can modulate autoimmunity have been considered as potential therapies for treating T cell-mediated autoimmune diseases and chronic inflammatory diseases. However, the inconvenience of intravenous (IV) administration, as well as the high costs and adverse events, including anemia, neutropenia and thrombocytopenia, associated with conventional therapies prevent their wide use as first-line medications.

Multiple sclerosis is an auto-immune disease of the Central Nerve System (CNS) associated with abnormal inflammatory response, chronic demyelination and axonal loss. MS lesions can be repaired by endogenous oligodendrocyte precursor cells (OPCs), but in most cases, re-myelination does not occur or is insufficient, leading to chronic disability. Current MS treatments are mostly immunosuppressive drugs that have minimal effect in regeneration of CNS myelin and in the reversal of the disease symptoms and damaging effects. Therefore, development of therapies promoting not only immunosuppressive effects but also re-myelination would represent an important advance in MS treatment but also in a variety of autoimmune and inflammatory diseases in which immune cells or cytokines are involved in the damage of specific tissues, including type 1 diabetes, HIV, rheumatoid arthritis, atopic dermatitis, ulcerative colitis, Crohn's disease, psoriasis, Parkinson's disease, irritable bowel syndrome, asthma, and hepatitis.

Accordingly, there is a need for improved methods for treating autoimmune and inflammatory diseases and in particular, multiple sclerosis.

SUMMARY

The present invention solves one or more problems of the prior art by providing in at least one embodiment a method for alleviating a symptom of and/or treating an autoimmune disease in part by reducing/preventing/reversing autoimmunity and inflammation and in part by promoting regeneration. The method includes a step of identifying a subject having an autoimmune or inflammatory disease. A FASTING MIMICKING DIET™ is administered to the subject for a first predetermined time period. The FASTING MIMICKING DIET™ is a calorie restricted diet and/or a ketogenic diet typically with proteins/amino acids and carbohydrates being restricted but otherwise providing high micronutrient nourishment. A non-fasting diet is administered to the subject for a second time period following the first time period. The non-fasting diet provides the subject a normal or even elevated calorie intake necessary to return to the normal and healthy weight.

In another embodiment, a method for alleviating a symptom of and/or treating multiple sclerosis or another autoimmune/inflammatory disease is provided. The method includes a step of identifying a subject having a multiple sclerosis or another autoimmune/inflammatory disease. A FASTING MIMICKING DIET™ is administered to the subject for a first predetermined time period, the FASTING MIMICKING DIET™. The FASTING MIMICKING DIET™ is a calorie restricted diet and/or a ketogenic diet typically with protein and carbohydrate being restricted. A non-fasting diet is administered to the subject for a second time period following the first time period. The non-fasting diet provides the subject a normal or even elevated calorie intake necessary to return to the normal and healthy weight.

In yet another embodiment, a method for alleviating a symptom of and/or treating T-cell or cytokine-mediated disease is provided. The method includes a step of identifying a subject having a T-cell or cytokine-mediated disease. A FASTING MIMICKING DIET™ is administered to the subject for a first predetermined time period. The FASTING MIMICKING DIET™ is a calorie restricted diet and/or a ketogenic diet typically with proteins/amino acids and carbohydrates being restricted but otherwise providing high micronutrient nourishment. A non-fasting diet is administered to the subject for a second time period following the first time period. The non-fasting diet provides the subject a normal or even elevated calorie intake necessary to return to the normal and healthy weight.

BRIEF DESCRIPTION OF THE DRAWINGS

FIG. 1 provides Table 1 showing FMD-altered T cell populations and cytokines as therapeutic targets for treating major autoimmune diseases and chronic inflammatory diseases.

DETAILED DESCRIPTION

Reference will now be made in detail to presently preferred compositions, embodiments and methods of the present invention. The Figures are not necessarily to scale. The disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

This invention is not limited to the specific embodiments and methods described below, as specific components and/or conditions may, of course, vary. Furthermore, the terminology used herein is used only for the purpose of describing particular embodiments of the present invention and is not intended to be limiting in any way.

As used in the specification and the appended claims, the singular form "a," "an," and "the" comprise plural referents unless the context clearly indicates otherwise. For example, reference to a component in the singular is intended to comprise a plurality of components.

The terms "kilocalorie" (kcal) and "Calorie" refer to the food calorie. The term "calorie" refers to the so-called small calorie.

The term "subject" refers to a human or animal, including all mammals such as primates (particularly higher primates), sheep, dog, rodents (e.g., mouse or rat), guinea pig, goat, pig, cat, rabbit, and cow.

The "term FASTING MIMICKING DIET™" means a diet that provides the subject with a calorie restricted diets formulated in a way to generate changes in glucose, ketone bodies, IGF-1 and IGFBP1 similar to those caused by fasting but able to provide high nourishment and minimize hunger.

Abbreviations:

"AL" mean ad lib.

"DAPI" means 4',6-diamidino-2-phenylindole which is a fluorescent stain.

"EAE" means experimental autoimmune encephalomyelitis.

"FMD" means FASTING MIMICKING DIET™.

"KB" means ketone bodies.

"KD" means ketogenic diet.

"MOG35-55" means myelin oligodendrocyte glycoprotein.

"MS" means multiple sclerosis.

"STZ" means streptozotocin.

An embodiment, a method for alleviating a symptom of an autoimmune or inflammatory disease in part by reducing/preventing/reversing autoimmunity and inflammation and in part by promoting regeneration is provided. The method includes a step of identifying a subject having an autoimmune or inflammatory disease. A FASTING MIMICKING DIET™ is administered to the subject for a first predetermined time period. In one variation, the FMD diet reduces the subject's serum concentration of IGF-I by 25-90% and the blood glucose concentration by 25-75%. Examples of FMD diets that can be used in the present invention are found in U.S. patent application Ser. Nos. 14/060,494 and 14/178,953; the entire disclosures of which are hereby incorporated by reference. In one refinement, the FASTING MIMICKING DIET™ provides less than 60% of the subject's normal caloric intake with proteins/amino acids and carbohydrates being restricted. In a refinement, the FASTING MIMICKING DIET™ provides less than 100 grams of carbohydrates and less than 30 g of sugar per day and less than 28 g of proteins/amino acids per day. In another refinement, the FASTING MIMICKING DIET™ is a ketogenic diet with or without caloric restriction as set forth herein. A useful ketogenic diet will provide 52.4-82.4% fat, 10-16.6% carbohydrates, and 8-15% protein of total daily caloric intake.

In a variation, a non-fasting diet is administered to the subject for a second time period following the first time period as set forth below. In some refinements, the non-fasting diet provides the subject with normal or even elevated caloric intake necessary to return to the normal and healthy weight. The methods of the invention are useful for treating any subject afflicted with an autoimmune disease and in particular, humans and other mammals. A normal caloric intake is the number of calories a subject consumes to maintain the subject's weight. Typically, a normal caloric intake is from about 1600 to 2400 Calories (i.e., kilocalories) per day. In a refinement, a normal caloric intake is from 1800 to 2200 kilocalories.

In a variation, the methods of the invention are used for treating T-cell mediated diseases including autoimmune diseases and chronic inflammatory diseases in a subject. In this variation, method includes a step of identifying a subject having a T-cell mediated disease. A FASTING MIMICKING DIET™ is administered to the subject for a first predetermined time period, the FASTING MIMICKING DIET™ providing less than 60% of the subject's normal caloric intake with protein and carbohydrates being restricted. In a refinement, the FASTING MIMICKING DIET™ provides less than 100 grams of carbohydrates with less than 30 g of sugar per day and less than 28 g of proteins/amino acids per day. In a further refinement, the FASTING MIMICKING DIET™ provides less than 20 g sugar per day. In each of these refinements, the balance of the calories are from fat. In a variation, a non-fasting diet is administered to the subject for a second time period following the first time period as set forth below in more detail. In a refinement, the methods alter the numbers of pathogenic T cells and the levels of circulating cytokines to alleviate the severity of autoimmune insults as well as reduces markers that are highly associated with inflammatory diseases including EAE induced multiple sclerosis (MS) and in STZ induced type 1 diabetes (T1D) mouse models. For example, the method can decrease the numbers of $CD4^+$ and $CD8^+$ T cells by at least 20 percent and the level of circulating cytokines by at least 20 weight percent. In some refinements, the method can decrease the numbers of $CD4^+$ and $CD8^+$ T cells by at least 30 percent, 40 percent or 50 percent. In other refinements, the method can decrease the level of circulating cytokines by at least 30 weight percent, 40 weight percent or 50 weight percent. Furthermore, at least some variations of the methods stimulate regeneration of undifferentiated precursor Cycles of the FMD alleviate autoimmune/inflammatory diseases such as multiple sclerosis and type 1 diabetes, in part, by reducing the number of circulating T lymphocytes and the insults caused by the pathogenic T cells. FMD reduces markers that are associated with inflammatory diseases i.e. TNF alpha, T cells, and C—reactive protein. This high efficiency, broad effects on T cell populations and inflammatory markers with minimal initial requirements and long-term safety/benefits allow the methods of the present invention to be incorporate into various types of therapy, including those involving biological and pharmaceutical therapies. Overall, FMD poses a great potential in both preventive and treatments for autoimmune/inflammatory diseases, demonstrated here in different but similar diseases shown here: type 1 diabetes, multiple sclerosis, and inflammatory dermatitis; therefore, the FMD treatment is widely applicable for treatment of other autoimmune/inflammatory diseases. With no need of invasive approach, it can benefit the conventional immunoregulatory approach in the way that directly regulates the T cells populations and/or may indirectly change the cytokines to ameliorate the inflammatory autoimmune insults. Here we show that the FASTING MIMICKING DIET™ (FMD) as an intensive but brief form of restriction of specific nutrient able to mimic fasting while preventing malnourishment can alter the numerical and functional profiles of T cell populations and levels of circulating cytokines which are key therapeutic targets of majority of autoimmune as well as reduces markers associated with inflammatory diseases (Table 1). Table 1 provides examples of diseases and conditions that can be treated with the methods of the invention. It is also demonstrated that the FMD promotes regeneration of oligodendrocytes in the MS and Type I diabetes model. Cycles of the FMD also increase regeneration of oligodendrocytes in MS by promoting differentiation of a precursor cells (oligodendrocyte precursor cells) to increases in functional cell types (oligodendrocytes). FMD is preferred over 120-hr fasting since it is extremely difficult for human subjects successfully fast due to low compliance and side-effects of malnutrition. Advantageously, the present invention using substitution diets, which maximize the micronutrient without interfering the beneficial effect of fasting condition in re-modulating immune systems and promoting regeneration.

In at least one embodiment, a method for treating, alleviating, and preventing recurrence of a symptom of multiple sclerosis (MS) is provided. The method includes a step of identifying a subject having a diagnosis of a multiple sclerosis or exhibiting one or more symptoms of multiple sclerosis. Examples of symptoms of multiple sclerosis include, but are not limited to, neurological dysfunction (e.g., autonomic, visual, motor, and sensory dysfunction), muscle weakness, muscle spasms, depression, mood swings, nervous system lesions (e.g., sclera), demyelination, etc. The subject is periodically administered a FASTING MIMICKING DIET™ (FMD) as set forth herein to treat or alleviate a symptom of multiple sclerosis. For example, in a refinement, the FASTING MIMICKING DIET™ provides less than 60% of the subject's normal caloric intake with proteins/amino acids and carbohydrates being restricted. In a further refinement, the FASTING MIMICKING DIET™ provides less than 100 grams of carbohydrates and less than 30 g of sugar per day and less than 28 g of proteins/amino acids per day. In another refinement, the FASTING MIMICKING DIET™ is a ketogenic diet with or without caloric restriction as set forth herein. A useful ketogenic diet will provide 52.4-82.4% fat, 10-16.6% carbohydrates, and 8-15% protein of total daily calorie intake.

In a variation of the methods set forth above, the FASTING MIMICKING DIET™ provides the subject less than 80 percent, 70 percent, 60 percent, 50 percent, 45 percent, 40 percent, or 35 percent of the subject's normal caloric intake. In still other refinements, the FASTING MIMICKING DIET™ provides the subject with greater than, in increasing order of preference, 10%, 20%, 25% or 30% of the subject's normal caloric intake. In a refinement, the FMD is administered for a first predetermined time period. Typically, the FASTING MIMICKING DIET™ provides the subject with less than 30 g of sugar per day, less than 28 g of proteins per day, 20-30 grams of monounsaturated fats per day, 6-10 g of polyunsaturated fats per day, and 2-12 g of saturated fats per day. In a refinement, the FASTING MIMICKING DIET™ provides less than 25 g of sugar, less than 23 g of proteins, 16-25 grams of monounsaturated fats, 4.8-8 g of polyunsaturated fats and 1-10 g of saturated fats. In another refinement, the FASTING MIMICKING DIET™ provides the subject with less than 20 g of sugars per day, less than 18 g of protein per day, 10-15 g of monounsaturated fats per day, 3-5 g of polyunsaturated fats per day and 1-6 grams of saturated fats per day. In still another refinement, the FASTING MIMICKING DIET™ provides less than 16 g of sugars, less than 15 g of protein, 8-12 g of monounsaturated fats, and 2-4 g of polyunsaturated fats and 1-6 grams of saturated fats. Typically, the FASTING MIMICKING DIET™ provides 100% of the recommended daily allowance (RD) for vitamins, minerals, and essential fatty acids.

In a variation of the methods set forth above, the first time period is from 3 to 30 days. In another variation of the methods set forth above, the first time period is from 3 to 7 days. In a refinement, the first time period is about 1 or 2 or 3 or 4 or 5 or 6 or 7 days. In another variation of the methods set forth above, the first time period is from 3 to 7 days. In a refinement, the first time period is about 1 or 2 or 3 or 4 or 5 or 6 or 7 days. In a further refinement, the first time period is about 5 days. Typically, the FASTING MIMICKING DIET™ is periodically administered to the subject. In one variation, the FASTING MIMICKING DIET™ is administered to the subject at 4-16 week time intervals. In another variation, the FASTING MIMICKING DIET™ can be administered to the subject at 2 to 4 week time intervals. In a variation, the subject is provided with 4.5-7 kilocalories per pound of the subject on a first day of the FASTING MIMICKING DIET™. In a refinement, the subject is provided with 3.5-5 kilocalories per pound of the subject on a first day of the FASTING MIMICKING DIET™. For days 2-5 of the FASTING MIMICKING DIET™ of this variation, the subject is provided with 3-5 kilocalories per pound of the subject's weight. 14. In a variation when the FASTING MIMICKING DIET™ is administered for 4 days, the FASTING MIMICKING DIET™ provides 2.4 to 4 kilocalories per pound of the subject for days 2-4.

In a variation of the methods set forth above, the FMD is alternated with a non-fasting diet (non-FD) in order to allow subject to regain normal weight. Typically, the non-FD is administered on the day after completion of a cycle of the FMD. In a refinement, the non-FD is administered 1-7 days (e.g., 1, 2, 3, 4, 5, 6 or 7 days) after completion of a cycle of the FMD. The non-FD diet provides the subject with normal caloric intake. The non-FD is administered for a second time period. Typically, the second period of time is from 1 day to 55 days. In a refinement, the second period of time is greater than or equal to, in increasing order of preference, 1 day, 3 days, 7 days, 14 days, or 20 days. In another refinement, the second period of time is from 1 day to 55 days. In a refinement, the second period of time is less than or equal to, in increasing order of preference, 60 days, 50 days, 40 days, 30 days, or 25 days. In a variation, the FMD and the non-FD are administered to the subject every 2 to 4 weeks over a period of treatment. In another variation, the FMD and the non-FD are administered to the subject every 2 to 8 weeks over a period of treatment. A period of treatment is typically from a month to several years or for the lifetime of the subject.

The following FASTING MIMICKING DIET™s (FMDs) and method will be required to effectively treat multiple sclerosis and to prevent relapsing remitting multiple sclerosis. They were developed by extrapolating from the mouse diet (see figures), based on calorie intake compared to normal/ad lib intake and macronutrient and micronutrient composition (compared to the standard composition) and using human data from an ongoing clinical trial that reaches the fold change ranges of the concentrations of glucose, ketone bodies, IGF-I level and IGFBP-1 level similar to the mouse diet and that affect the anti-inflammatory corticosteroids and inflammatory markers.

The following examples illustrate the various embodiments of the present invention. Those skilled in the art will recognize many variations that are within the spirit of the present invention and scope of the claims.

The substitution diets are scaled for mice in the experiments set forth below. For both treating and reversing autoimmune/inflammatory diseases, either Diet 1 or Diet 2 can be given to the subjects and the frequency of the cycle should be decided based on the ability of subjects to regain the normal body weight and/or the physician's recommendation to be a healthy weight—BMI of at least 18 or higher.

It has been shown that the FMD cycles decrease glucose and serum IGF-1 level. A decrease in serum IGF-1 level has been shown to be one of the biomarkers that indicate regeneration effects and an increase in stems and and/or progenitor cells in hematopoietic stem cell in both mice and human (Cheng et al., 2014 Cell Stem Cell; patent pending). In 10 week old female C57B1/6 mice, one cycle of FMD) reduced the bodyweight by 18% compared to controls and significantly reduced glucose level and serum IGF-1 level. Upon re-feeding, FMD recovered to its normal body weight. In a similar manner, an on-going clinical trial in humans has also shown that a single cycle of the analogous FMD (adjusted for weight and other requirements specific for humans) shows reduced blood glucose level as well as serum IGF-I levels. Moreover, IGFBP-1, which binds and reduces the bioavailability of IGF-1, significantly increased upon a single FMD cycle to contribute further to the inhibition of IGF-I signaling.

The experimental mouse FMD is based on a nutritional screen that identified ingredients, which allow high nourishment during periods of low calorie consumption. The mouse FMD diet consists of two different components designated as day 1 diet and day 2-3 diet that were fed in this order respectively. Day 1 diet contains 7.87 kJ/g and the day 2-3 diet is identical on all feeding days and contains 1.51 kJ/g. Day 1 and day 2-3 diets were supplied to the FMD cohort with the average intake of the ad lib control group (~4 g) every two weeks. On average, mice consumed 11.07 kJ (plant-based protein 0.75 kJ, carbohydrate 5.32 kJ, fat 5 kJ) on each day of the FMD regimen. In both the MS and T1D models, we supplied TD.7912 chow ad lib for 4 to 7 days after the end of the day 2-3 diet. The duration of FMD and that of refeeding with TD.7912 may be adjusted by the body weight loss (≤20%) and recovery (≥95%). In the case of MS model, the refeeding period was limited to 4 days. Prior to supplying the FMD diet, animals were transferred into fresh cages to avoid feeding on residual chow and coprophagy. The experimental mouse KD contains 0.34 kcal/gm of protein, 6.76 kcal/gm of fat and 0.13 kcal/gm of carbohydrates.

Modified Human FASTING MIMICKING DIET™ 1: The FMD will substitute a subjects' normal diet for a period of 5 to 7 days (see below) every 4-16 weeks depending on the types and severity of the subjects' disease condition and ability of the patient to regain weight before the next cycle is initiated. Patients with more severe symptoms who are able to regain weight will receive the diet every 4 weeks and patients with milder forms of the disease will receive the diet every 8-16 weeks. The FMD consists of ingredients, which are Generally Regarded As Safe (RGAS). Calories are consumed according to the subject's body weight. For day 1, total calorie consumption is 18.8-29.2 kJ (4.5-7 kcal) per pound (or 42-67 kJ per kilogram). The daily diet should contain less than 100 grams of carbohydrates with less than 30 g of sugars, less than 28 g of proteins/amino acids, 20-30 grams of monounsaturated fats, 6-10 g of polyunsaturated fats and 2-12 g of saturated fats. For days 2-5 or 2-7, total calorie consumption is 12.5-20.9 kJ (3-5 kcal) per pound (or 29-46 kJ per kilogram). The diet should contain less than 100 grams of carbohydrates with less than 20 g of sugars, less than 18 g of proteins/amino acids, 10-15 g of monounsaturated fats, and 3-5 g of poly unsaturated fats and 1-6 grams of saturated fats. Diet should also be high nourishment containing 100% of the RDA for vitamins, minerals+ essential fatty acids.

Modified Human FASTING MIMICKING DIET™ 2: The FMD will substitute a subjects' normal diet for a period of 4 days (see below) every 4-16 weeks depending on the types and severity of the subjects' disease condition and ability of the patient to regain weight before the next cycle is initiated. Patients with more severe symptoms who are able to regain weight will receive the diet every 2 weeks and patients with milder forms of the disease will receive the diet every 4 weeks. The FMD consists of ingredients, which are Generally Regarded As Safe (RGAS). Calories are consumed according to the subject's body weight. For day 1, total calorie consumption is 18.8-29.2 kJ (4.5-7 kcal) per pound (or 42-67 kJ per kilogram). The daily diet should contain less than 100 grams of carbohydrates with less than 25 g of sugar, less than 23 g of proteins/amino acids, 16-25 grams of monounsaturated fats, 4.8-8 g of polyunsaturated fats and 1-10 g of saturated fats. For days 2-4, total calorie consumption is 10-16.7 kJ (2.4-4 kcal) per pound (or 22.2-36.8 kJ per kilogram). The diet should contain less than 100 grams of carbohydrates, with less than 16 g of sugars, less than 15 g of proteins/amino acids, 8-12 g of monounsaturated fats, and 2-4 g of polyunsaturated fats and 1-6 grams of saturated fats. Diet should also be high nourishment containing 100% of the RDA for vitamins, minerals+essential fatty acids.

Modified Human Ketogenic Diet: The KD will substitute a subjects' normal diet continuously until subjects' disease conditions persist. Ketogenic diet should contain food source majority coming from mono-poly unsaturated fats and saturated fats. Briefly, the ketogenic diet should contain 52.4-82.4% fat, 10-16.6% carbohydrates, and 8-15% protein of total daily calorie intake. Diet should also be high nourishments containing 100% of RDA for vitamins, minerals and essential fatty acids.

Figure 2:
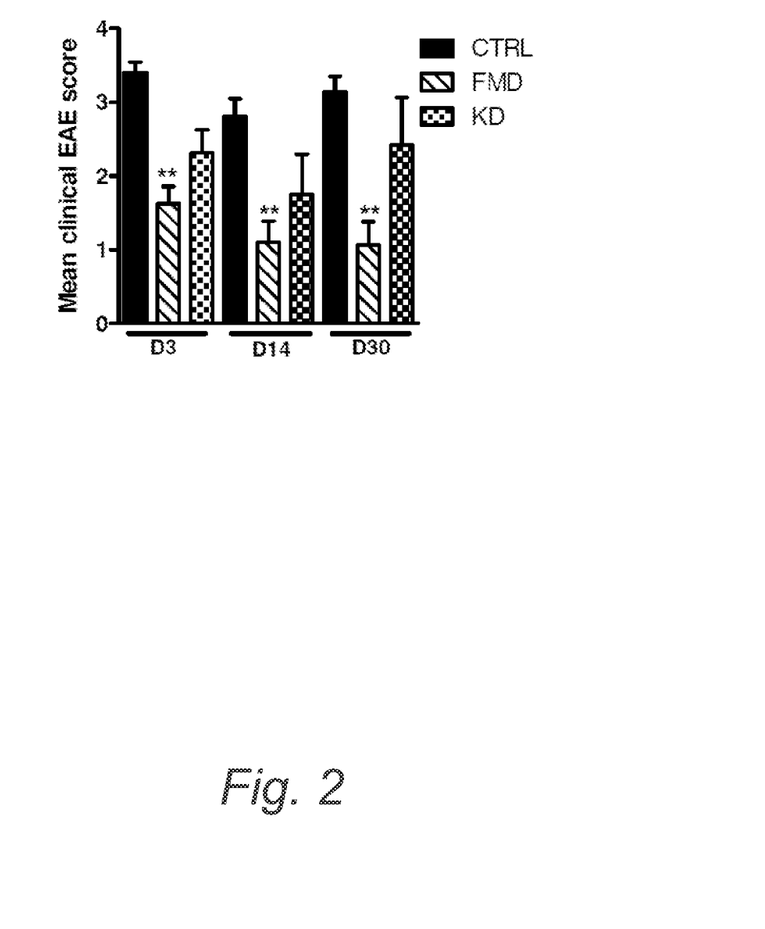
FIG. 2 is a bar chart showing the mean clinical EAE severity score of the FASTING MIMICKING DIET™ (FMD) treated mice of MOG$_{35-55}$ induced EAE MS mouse model.

FIG. 2 provides a bar chart showing the mean clinical EAE severity score of the FASTING MIMICKING DIET™ (FMD) treated mice of $MOG_{35-55}$ induced EAE MS mouse model. Experimental autoimmune encephalomyelitis is the most commonly used rodent experimental model for human multiple sclerosis. It is shown that periodic cycles of a FASTING MIMICKING DIET™ (FMD) (3 days of FMD and 4 days of ad libitum per week) have the therapeutic effects in $MOG_{35-55}$ induced EAE C57Bl/6 mice model of multiple sclerosis as well as reduction of autoimmunity and prevention of relapse of the disease. Weekly Cycles of FASTING MIMICKING DIET™ (FMD) lead to significantly reduced EAE severity scores (0—no observable symptom and 5—moribund) compared to the control diet (CTRL). A continuous ketogenic diet (KD) showed reduced EAE severity compared to the control but not to the extent of FMD.

Cycles of substitution diets reduced T cell populations and cytokines associated with symptoms of autoimmune diseases and alleviated the symptoms in the mouse models of multiple sclerosis (MS) and type 1 diabetes (T1D) in vivo. Table 2 provides results showing that FMD reduces splenic $CD4^+$ and $CD8^+$ T cells in mouse model of MS at the end of three days of FMD

TABLE 3

FMD reduces splenic $CD4^+$ $CD8^+$ T cells.

| Numbers (×10$^6$) | CTRL | FMD |
|---|---|---|
| CD4 | 1.52 ± 0.09 | 0.81 ± 0.16 ↓** |
| CD8 | 1.07 ± 0.16 | 0.60 ± 0.16 ↓* |
| Active CD4 | 0.81 ± 0.04 | 0.48 ± 0.09 ↓** |
| Active CD8 | 0.56 ± 0.01 | 0.35 ± 0.53 ↓** |

*p < 0.05,
***p < 0.01.
FMD, at the end of 3 d FMD)

Table 3 shows that FMD promotes oligodendrocyte precursors and differentiated oligodendrocytes at the spinal cord lesion of mouse model of MS. NG2 is used as a marker for the undifferentiated oligodendrocyte precursor cells. BrdU is used as a marker for proliferation. GSTπ is used as a marker for differentiated oligodendrocyte. $BrdU^+$ $GST\pi^+$ cells indicate that newly proliferated precursor cells that are differentiated to myelinating functional oligodendrocytes as a marker for regeneratio. FMD treatment shows an increase in NG2+ oligodendrocytes precursor cells and $GST\pi^+$ matured oligodendrocytes in the spinal cord lesion. The FMD mediated increase in both precursor and differentiated oligodendrocytes is due to increase in proliferation ($BrdU^+$ cells) that are successfully differentiated to mature oligodendrocytes ($BrdU^+$ $GST\pi^+$). These changes demonstrate regeneration at the lesion site

TABLE 3

FMD promotes oligodendrocyte precursors and differentiated oligodendrocytes.

| Fold-change from control | CTRL | FMD |
|---|---|---|
| NG2$^+$ Oligodendrocyte Precursor | 1.00 ± 0.31 | 1.21 ± 0.28 ↑ |
| Oligodendrocytes | 1.00 ± 0.047 | 1.44 ± 0.23 ↑* |
| BrdU$^+$ GSTπ$^+$ cells (Newly proliferated and differentiated oligodendrocytes) | 1.00 ± 0.26 | 1.94 ± 0.28 ↑↑* |

Figure 3:
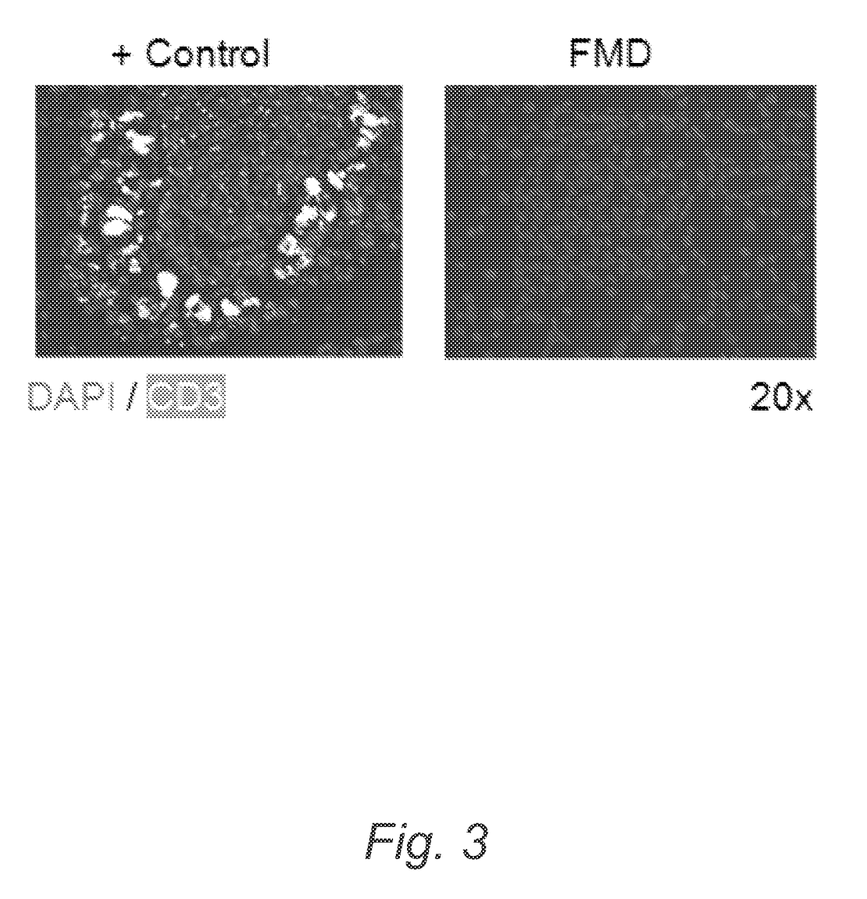
FIG. 3 shows fluorescent staining of pancreatic tissue demonstrating that observed that pancreas-infiltrating T cells (CD3+) were greatly reduced by cycles of FMD.

FIG. 3 shows fluorescent staining of pancreatic tissue. It was observed that pancreas-infiltrating T cells (CD3+) were greatly reduced by cycles of FMD. Table 4 demonstrates that FMD alleviates pathogenic autoimmune responses in STZ induced type I diabetes. Table 4 shows that FMD reduces levels of circulating cytokines associated with β-cell insults

TABLE 4

FMD reduces circulating cytotoxic $CD8^+$ T cells.

|  | d 0 | FMD | post-FMD |
|---|---|---|---|
| Total T cells | 1.03 ± 0.20 | 0.58 ± 0.10 ↓* | 0.35 ± 0.14 ↓↓* |
| % of cytotoxic T cells | 39.54 ± 5.07 | 43.03 ± 6.70 — | 14.52 ± 3.76 ↓↓** |
| cytotoxic T cells | 2.62 ± 0.34 | 1.34 ± 0.17 ↓↓* | 2.18 0.30 ↓* |

*p < 0.05,
***p < 0.005.
FMD, at the end of 4 d FMD; post-FMD, 3 days after refeeding.

TABLE 4

FMD reduces levels of circulating cytokines

|  | STZ | FMD + STZ |
|---|---|---|
| TNFα | 0.52 ± 0.28 | −0.10 ± 0.14↓↓ |
| MCP-1 | 2.02 ± 1.02 | 0.35 ± 0.62↓↓ * |
| IL-12 | 0.09 ± 0.16 | −0.31 ± 0.12↓↓*** |
| RANTES | 0.00 ± 0.06 | −0.45 ± 0.07↓↓ * |

* p < 0.05,
***p < 0.005.
FMD, at the end of 4 d FMD.

Figure 4:
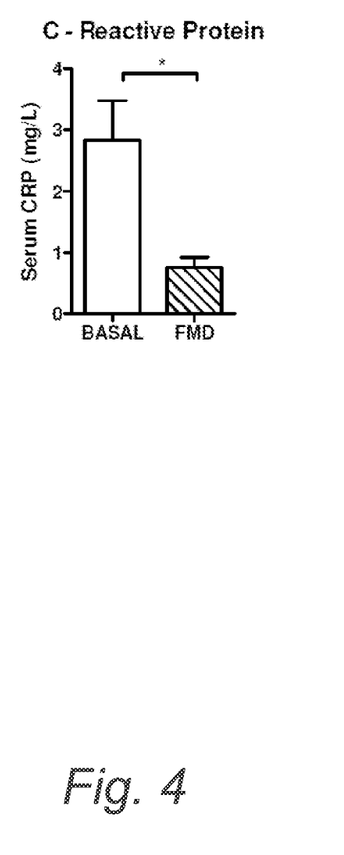
FIG. 4 is a bar chart showing that FMD reduces levels of circulating C-reactive protein in a pilot human trials (*p<0.05; n=5).

FIG. 4 is a bar chart showing that FMD reduces serum CRP level and increase cortisol level in a human trial. CRP is known to be one of the main markers for inflammatory diseases. FMD treatment shows 3-fold decrease in CRP level in a human clinical trial.

Figure 5:
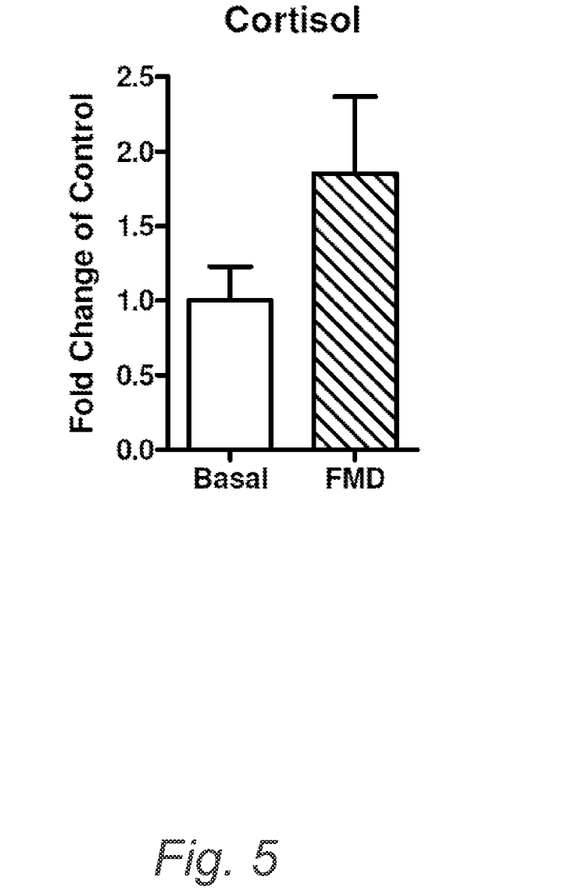
FIG. 5 is a bar chart showing that the FMD increases levels of circulating Cortisol in a pilot human trials (*p<0.05; n=5).

FIG. 5 shows that the FMD increases levels of circulating Cortisol in a human clinical trial. (*p<0.05; n=5). Cortisol is in a class of glucocorticoids that are known to be anti-inflammatory by interfering T-cell proliferation and activation as well as decreasing a wide variety of cytotoxic cytokines including TNFalpha. FMD treatment shows a near 2-fold increase in cortisol level compared to the control in a human clinical trial.

Cycles of substitution diet showed 2-fold reduction (20% in control cohort vs. 10% in FMD cohort) in dermatitis incidence in wild-type C57B1/6 mice as summarized in Table 5.

TABLE 5

FMD reduces rate of spontaneous dermatitis incidence

|  | Control | FMD |
|---|---|---|
| % incidence | 20 | 10 ↓* |

*p < 0.05.

Table 6 shows that the percentage of disease-induced mice recovered/showed improvement from type 1 diabetes STZ autoimmune model and MS EAE autoimmune model.

TABLE 6

50-100% improvement of Type 1 diabetes and multiple sclerosis symptoms in mice treated with an FMD diet

|  | Control | FMD |
|---|---|---|
| Type 1 Diabetes (STZ model) | 0% | 100% |
| Multiple Sclerosis (EAE model) | 0% | 52.7% |

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for alleviating a symptom of autoimmunity, the method comprising:
   identifying a subject having an autoimmune disease;
   administering a first diet to the subject for a first predetermined time period of three to seven days, the first diet providing less than 100 grams of carbohydrates with less than 30 g of sugars per day and less than 28 g of proteins/amino acids per day, the first diet providing greater than 30 percent of the subject's normal caloric intake and less than 50% of the subject's normal caloric intake, with 52.4 to 82.4% of the total daily caloric intake being fat, 10 to 16.6% of the total daily caloric intake being carbohydrates, and 8-15% of the total daily caloric intake being protein, the first diet also providing 10-15 g of monounsaturated fats per day, 3-5 g of polyunsaturated fats per day and 1-6 grams of saturated fats per day; and
   administering a non-fasting diet to the subject for a second time period of three to sixteen weeks following the first predetermined time period, the non-fasting diet providing the subject with normal caloric intake, the normal caloric intake being the number of calories the subject consumes to maintain the subject's weight.

2. The method of claim 1 wherein the first diet is a ketogenic diet.

3. The method of claim 1 wherein the first predetermined time period is about 5 days.

4. The method of claim 3 wherein on a first day of the first predetermined time period of the first diet, the subject is provided with 4.5-7 kilocalories per pound of the subject.

5. The method of claim 3 wherein for each day on days 2-5 of the first diet the subject is provided with 3-5 kilocalories per pound of the subject's weight.

6. The method of claim 4 wherein the first predetermined time period of the first diet provides the subject with less than 100 grams of carbohydrates and less than 20 g of sugars per day, and less than 18 g of proteins/amino acids per day.

7. The method of claim 1 wherein the first predetermined time period is about 4 days.

8. The method of claim 7 wherein on a first day of the first predetermined time period of the first diet, the subject is provided with 3.5-5 kilocalories per pound of the subject.

9. The method of claim 8 wherein for each day from days 2-4 the first diet provides 2.4 to 4 kilocalories per pound of the subject.

10. The method of claim 1 wherein the subject is a mammal.

11. The method of claim 1 wherein the subject is a human.

12. The method of claim 1 wherein the autoimmune disease is multiple sclerosis.

13. A method for treating multiple sclerosis comprising:
   identifying a subject having multiple sclerosis;
   administering a first diet to the subject for a first predetermined time period of three to seven days, the first diet providing greater than 30 percent of the subject's normal caloric intake and less than 50% of the subject's normal caloric intake restricting both proteins/amino acid and carbohydrate intake to less than 30 g of sugars per day and less than 28 g of proteins per day, the first diet also providing 10-15 g of monounsaturated fats per day, 3-5 g of polyunsaturated fats per day and 1-6 grams of saturated fats per day, the subject's normal caloric intake being the number of calories the subject consumes to maintain the subject's weight; and
   administering a non-fasting diet to the subject for a second time period of three to sixteen weeks following the first predetermined time period, the non-fasting diet providing the subject greater than 60 percent of the subject's normal caloric intake but a calorie intake necessary for the subject to return to a normal healthy weight.

14. A method for treating T-cell mediated disease comprising:
   identifying a subject having;
   administering a first diet to the subject for a first predetermined time period of three to seven days, the first diet providing greater than 30 percent of the subject's normal caloric intake and less than 50% of the subject's normal caloric intake restricting both protein/amino acids and carbohydrate intake to less than 30 g of sugars per day and less than 28 g of proteins/amino acids per day, the first diet also providing 10-15 g of monounsaturated fats per day, 3-5 g of polyunsaturated fats per day and 1-6 grams of saturated fats per day; and
   administering a non-fasting diet to the subject for a second time period of three to sixteen weeks following the first predetermined time period, the non-fasting diet providing the subject greater than 60 percent of the subject's normal caloric intake but a calorie intake necessary for the subject to return to a normal healthy weight, the subject's normal caloric intake being the number of calories the subject consumes to maintain the subject's weight.

15. The method of claim 14 wherein the T-cell mediated disease is an autoimmune disease.

16. A method for alleviating a symptom of autoimmunity, method comprising:

identifying a subject having an autoimmune disease;

administering a first diet to the subject for a first predetermined time period of three to seven days, the first diet being a ketogenic diet, the first diet providing greater than 30 percent of the subject's normal caloric intake and less than 50% of the subject's normal caloric intake, with 52.4 to 82.4% of the total daily caloric intake being fat, 10 to 16.6% of the total daily caloric intake being carbohydrates, and 8-15% of the total daily caloric intake being protein, the first diet also providing 10-15 g of monounsaturated fats per day, 3-5 g of polyunsaturated fats per day and 1-6 grams of saturated fats per day; and administering a non-fasting diet to the subject for a second time period of three to sixteen weeks following the first predetermined time period, the non-fasting diet providing the subject with normal caloric intake, the normal caloric intake being the number of calories the subject consumes to maintain the subject's weight.

17. A method for alleviating a symptom of autoimmunity, the method comprising:

identifying a subject having an autoimmune or inflammatory disease;

administering a first diet to the subject for a first predetermined time period of 3 to 5 days, the first diet providing greater than 20 percent of the subject's normal caloric intake and less than 40% of the subject's normal caloric intake, the first diet providing less than 100 grams of carbohydrates with less than 30 g of sugars per day and less than 28 g of proteins/amino acids per day, the first diet also providing 10-15 g of monounsaturated fats per day, 3-5 g of polyunsaturated fats per day and 1-6 grams of saturated fats per day; and administering a non-fasting diet to the subject for a second time period of three to sixteen weeks following the first predetermined time period, the non-fasting diet providing the subject with 1600 to 2400 kilocalories per day.

18. A method for alleviating a symptom of autoimmunity, the method comprising:

identifying a subject having an autoimmune disease;

administering a first diet to the subject for a first predetermined time period of three to seven days, the first diet providing less than 100 grams of carbohydrates with less than 30 g of sugars per day and less than 28 g of proteins/amino acids per day, the first diet providing greater than 10 percent of the subject's normal caloric intake and less than 35% of the subject's normal caloric intake, with 52.4 to 82.4% of the total daily caloric intake being fat, 10 to 16.6% of the total daily caloric intake being carbohydrates, and 8-15% of the total daily caloric intake being protein, the first diet also providing 20-30 grams of monounsaturated fats per day, 6-10 g of polyunsaturated fats per day, and 2-12 g of saturated fats per day; and administering a non-fasting diet to the subject for a second time period of three to sixteen weeks following the first predetermined time period, the non-fasting diet providing the subject with normal caloric intake, the normal caloric intake being the number of calories the subject consumes to maintain the subject's weight.

19. A method for alleviating a symptom of autoimmunity, the method comprising:

identifying a subject having an autoimmune disease;

administering a first diet to the subject for a first predetermined time period of three to seven days, the first diet providing greater than 10 percent of the subject's normal caloric intake and less than 35% of the subject's normal caloric intake, the first diet providing less than 100 grams of carbohydrates with less than 25 g of sugars per day and less than 23 g of proteins/amino acids per day, the first diet providing less than 60% of the subject's normal caloric intake, with 52.4 to 82.4% of the total daily caloric intake being fat, 10 to 16.6% of the total daily caloric intake being carbohydrates, and 8-15% of the total daily caloric intake being protein, the first diet also providing 16-25 grams of monounsaturated fats per day, 4.8-8 g of polyunsaturated fats and 1-10 g of saturated fats per day; and administering a non-fasting diet to the subject for a second time period of three to sixteen weeks following the first predetermined time period, the non-fasting diet providing the subject with normal caloric intake, the normal caloric intake being the number of calories the subject consumes to maintain the subject's weight.

\* \* \* \* \*

UNITED STATES PATENT AND TRADEMARK OFFICE
CERTIFICATE OF CORRECTION

Page 1 of 1

PATENT NO. : 11,406,122 B2
APPLICATION NO. : 15/301480
DATED : August 9, 2022
INVENTOR(S) : Valter D. Longo et al.

It is certified that error appears in the above-identified patent and that said Letters Patent is hereby corrected as shown below:

In the Specification

Column 1, Line 16:
Delete:
"The invention was made with Government support under Contract No. PO1AGT034906 awarded by the National Institutes of Health/National Institute of Aging. The Government has certain rights to the invention."
And Insert:
-- This invention was made with government support under grant no. AG034906 awarded by the National Institutes of Health. The government has certain rights in the invention. --

Signed and Sealed this
Fourth Day of October, 2022

Katherine Kelly Vidal
*Director of the United States Patent and Trademark Office*